(12) United States Patent
Speckbacher et al.

(10) Patent No.: US 7,534,273 B2
(45) Date of Patent: May 19, 2009

(54) CATIONIC PYRAZOLONE DYES, METHOD FOR PRODUCTION THEREOF AND COLORING AGENTS FOR KERATIN FIBERS CONTAINING SAID COMPOUNDS

(75) Inventors: Markus Speckbacher, Gschaffenburg (DE); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 0 days.

(21) Appl. No.: 11/572,623

(22) PCT Filed: May 18, 2005

(86) PCT No.: PCT/EP2005/005399

§ 371 (c)(1),
(2), (4) Date: Oct. 3, 2007

(87) PCT Pub. No.: WO2006/012934

PCT Pub. Date: Feb. 9, 2006

(65) Prior Publication Data

US 2008/0263787 A1  Oct. 30, 2008

(30) Foreign Application Priority Data

Jul. 28, 2004  (DE) .................. 10 2004 036 609

(51) Int. Cl.
*A61Q 5/10* (2006.01)
*C07D 231/00* (2006.01)

(52) U.S. Cl. .................. 8/405; 8/426; 8/455; 8/552; 8/567; 8/570; 8/572; 8/573; 8/575; 548/356.1

(58) Field of Classification Search ................ 8/405, 8/426, 455, 552, 567, 570, 572, 573, 575; 548/356.1

See application file for complete search history.

(56) References Cited

U.S. PATENT DOCUMENTS 4,369,310 A 1/1983 Postle
2004/0034945 A1 2/2004 Javet et al.

FOREIGN PATENT DOCUMENTS

WO 95/01772 1/1995

OTHER PUBLICATIONS

STIC Search Report dated Sep. 9, 2008.*
A.I.M. Koraiem: "Apocyanine Dyes From 4,5 . . . " Journal Fuer Praktische Chemie, BD. 326, No. 5, 1984, pp. 811-816. (In English).
L. Knorr: "Liebigs Annalen Der Chemie", 1887, 238, pp. 137-219.

* cited by examiner

*Primary Examiner*—Eisa B Elhilo
(74) *Attorney, Agent, or Firm*—Michael J. Striker

(57) ABSTRACT

The present application relates to cationic pyrazolone dyes of the general formula (I),

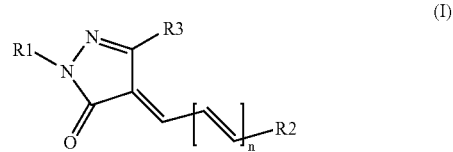

and to coloring agents for keratin fibers comprising these dyes.

11 Claims, No Drawings

CATIONIC PYRAZOLONE DYES, METHOD FOR PRODUCTION THEREOF AND COLORING AGENTS FOR KERATIN FIBERS CONTAINING SAID COMPOUNDS

CROSS REFERENCE TO RELATED APPLICATIONS

This application is the National Stage Entry of PCT/EP2005/005399, filed May 18, 2005, and claims priority under 35 U.S.C. 119(a)-(d) to German Patent Application DE 10204036609.8, filed Jul. 28, 2004.

The present invention relates to novel cationic pyrazolone dyes, to a method for production thereof, and to coloring agents containing said compounds for keratin fibers, in particular hair.

For coloring keratin-containing fibers, e.g. hair, wool or furs, use is generally made either of oxidation dyes, which arise as a result of oxidative coupling of one or more developer components with one or more coupler components, or direct dyes. If required, oxidation-stable, direct dyes can be added to the oxidative system in order to achieve particular color effects. Direct dyes are incorporated into suitable carrier masses in order then to be applied to the fibers. This method, generally known as tinting, is easy to use, exceptionally mild and is characterized by low damage to the keratin fiber if no ammonia or peroxide is added. However, the dyes used here have to satisfy a number of requirements. For example, they have to be acceptable from a toxicological and dermatological point of view and allow colorations to be achieved in the desired intensity and brilliance. Furthermore, for the colorations achieved, good fastness to light, resistance to shampooing and conditioners, and good fastness to rubbing is required.

For a nonoxidative coloring agent for keratin fibers based on direct dyes, a combination of different nonoxidative (direct) dyes is generally required in order to achieve certain nuances. Since the selection of such dyes which adequately satisfy the specified requirements is limited, there continues to be a great need for such dyes.

It is therefore an object of the present invention to provide direct dyes for coloring keratin fibers, in particular human hair, which satisfy these requirements in an excellent manner.

Surprisingly, it has now been found that cationic pyrazolone dyes of the general formula (I) as direct dyes in nonoxidative coloring agents permit very gentle coloring of keratin fibers.

The present invention therefore provides cationic pyrazolone dyes of the general formula (I),

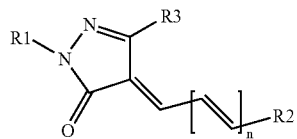
(I)

in which
n is 0 or 1;
$R_1$ and $R_2$, independently of one another, are one of the formulae (II), (III), (IV), (V) or (VI),

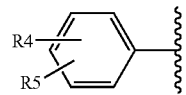
(II)

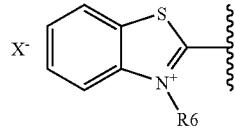
(III)

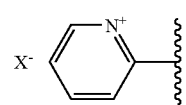
(IV)

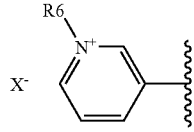
(V)

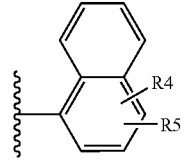
(VI)

$R_3$ is a $C_1$-$C_6$-alkyl group, a $C_1$-$C_6$-alkylcyano group, a hydroxyl group, a methoxymethyl group, a $C_1$-$C_6$—N,N-dialkylamino group, a carboxamide group, a $C_1$-$C_6$-alkylsulfonic acid group, a sulfonic acid group, a sulfonic acid ester group, a carboxylic acid group, a carboxylic acid ester group, an amino group, a sulfonamide group, a methyl group, an isopropyl group, a tert-butyl group or a phenyl group, preferably a carboxylic acid group, a carboxylic acid ester group or an amino group and in particular a methyl group;

$R_4$ is a hydrogen atom, a $C_1$-$C_6$-alkylamino group, a $C_1$-$C_6$—N,N-dialkylamino group, a $C_1$-$C_6$-alkylcyano group, a hydroxyl group, a nitro group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylsulfonic acid group, a $C_1$-$C_6$-alkylsulfonic acid ester group, or an —N-(L)-(L)-$B^+$ group;

$R_5$ is a hydrogen atom, a $C_1$-$C_6$-alkylamino group, a $C_1$-$C_6$—N,N-dialkylamino group, a $C_1$-$C_6$-alkylcyano group, a hydroxyl group, a nitro group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylsulfonic acid group, a $C_1$-$C_6$-alkylsulfonic acid ester group, an —N-(L)-(L)-$B^+$ group or a radical of the formulae (VII), (VIII) or (IX);

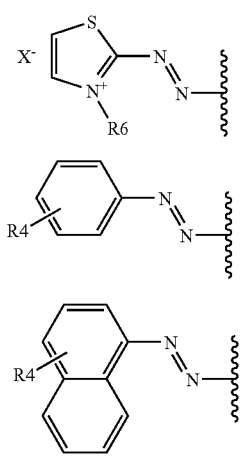

R₆ is a branched or linear $C_1$-$C_6$-alkyl group, a branched or linear $C_2$-$C_4$-hydroxyalkyl group or a branched or a linear $C_4$-$C_6$-polyhydroxyalkyl group;

L is a $C_1$-$C_6$-alkylene group;

B⁺ is the following radical groups a) an aromatic, heterocyclic quaternary ammonium compound, preferably a quaternary compound of N-methylimidazole, a quaternary compound of N-allylimidazole, a quaternary compound of 2-ethylimidazole, a quaternary compound of 1,2-dimethylimidazole, a quaternary compound of pyridine, a quaternary compound of 4-dimethylaminopyridine, a quaternary compound of pyrimidine, a quaternary compound of pyrazole, a quaternary compound of N-methylpyrazole or a quaternary compound of quinoline; or b) a nonaromatic heterocyclic quaternary ammonium compound, in particular a quaternary compound of N-methylmorpholine, a quaternary compound of N-ethylmorpholine or a quaternary compound of 1-methylpiperidine; or c) a quaternary alkylammonium compound or arylammonium compound of the formula $NR_aR_bR_c$, where $R_a$, $R_b$ and $R_c$, independently of one another, are a benzyl radical, a phenyl radical or a $C_1$- to $C_6$-alkyl radical, in particular a methyl radical, an ethyl radical, a propyl radical, an isopropyl radical or a butyl radical, where the abovementioned alkyl radicals may be unsubstituted or substituted by one or more hydroxyl groups or amino groups; or d) a quaternary phosphonium group, for example a tributylphosphonium group, but in particular a trimethylammonium group or a triethylammonium group; and X⁻ is an anion;

with the proviso that at least one of the radicals $R_1$ and $R_2$ is a cationic group.

The counterions X⁻ used are preferably the following anions: sulfate anions, phosphate anions, hydrogenphosphate anions, oxalate anions, formate anions, acetate anions, citrate anions, tartrate anions, malonate anions, pyruvate anions or iodide anions, where chloride anions, bromide anions and methylsulfate anions are particularly preferred.

Suitable cationic direct dyes of the general formula (I) which may be mentioned are, for example: 2-{(4E)-4-[4-(dimethylamino)benzylidene]-3-methyl-5-oxo-4,5-dihydro-1H-pyrazol-1-yl}-1-methylpyridinium methyl-sulfate, 2-{(4E)-4-[4-(dimethylamino)benzylidene]-3-methyl-5-oxo-4,5-dihydro-1H-pyrazol-1-yl}-3-methyl-1,3-benzothiazol-3-ium methylsulfate, 2-[(4E)-4-(4-hydroxybenzylidene)-3-methyl-5-oxo-4,5-dihydro-1H-pyrazol-1-yl]-1-methylpyridinium methylsulfate, 2-[(4E)-4-(4-hydroxybenzylidene)-3-methyl-5-oxo-4,5-dihydro-1H-pyrazol-1-yl]-3-methyl-1,3-benzothiazol-3-ium methylsulfate, 2-[(4E)-4-(4-hydroxy-3-methoxy-benzylidene)-3-methyl-5-oxo-4,5-dihydro-1H-pyrazol-1-yl]-1-methylpyridinium methylsulfate, 2-[(4E)-4-(4-hydroxy-3-methoxybenzylidene)-3-methyl-5-oxo-4,5-dihydro-1H-pyrazol-1-yl]-3-methyl-1,3-benzothiazol-3-ium methylsulfate, 2-((4E)-4-{[4-(dimethylamino)-1-naphthyl]methylene}-3-methyl-5-oxo-4,5-dihydro-1H-pyrazol-1-yl)-1-methylpyridinium methylsulfate, 2-((4E)-4-{[4-(dimethylamino)-1-naphthyl]methylene}-3-methyl-5-oxo-4,5-dihydro-1H-pyrazol-1-yl)-3-methyl-1,3-benzothiazol-3-ium methylsulfate, 2-((4E)-4-{4-hydroxy-3-[(E)-(4-methoxyphenyl)diazenyl]-benzylidene}-3-methyl-5-oxo-4,5-dihydro-1H-pyrazol-1-yl)-1-methylpyridinium methylsulfate, 2-((4E)-4-{4-hydroxy-3-[(E)-(4-methoxyphenyl)diazenyl]-benzylidene}-3-methyl-5-oxo-4,5-dihydro-1H-pyrazol-1-yl)-3-methyl-1,3-benzothiazol-3-ium methylsulfate, 2-((4E)-4-{4-hydroxy-3-[(E)-(4-nitrophenyl)diazenyl]-benzylidene}-3-methyl-5-oxo-4,5-dihydro-1H-pyrazole-1-yl)-1-methylpyridinium methylsulfate, 2-((4E)-4-{4-hydroxy-3-[(E)-(4-nitrophenyl)diazenyl]-benzylidene}-3-methyl-5-oxo-4,5-dihydro-1H-pyrazol-1-yl)-3-methyl-1,3-benzothiazol-3-ium methylsulfate, 1-methyl-3-{(E)-[3-methyl-1-(4-nitrophenyl)-5-oxo-1,5-dihydro-4H-pyrazol-4-ylidene]methyl}pyridinium methylsulfate, 3-{(E)-[1-(4-{(E)-[4-(dimethylamino)-phenyl]diazenyl}phenyl)-3-methyl-5-oxo-1,5-dihydro-4H-pyrazol-4-ylidene]methyl}1-methylpyridinium methyl-sulfate, 3-{(E)-[1-(4-methoxyphenyl)-3-methyl-5-oxo-1,5-dihydro-4H-pyrazol-4-ylidene]methyl}-1-methylpyridinium methylsulfate, 2-[4-{(4E)-4-[4-(dimethylamino)benzylidene]-3-methyl-5-oxo-4,5-dihydro-1H-pyrazol-1-yl}(ethyl)anilino]-N,N,N-trimethylethanaminium methylsulfate, 3-((E)-{1-[4-(diethylamino)phenyl]-3-methyl-5-oxo-1,5-dihydro-4H-pyrazol-4-ylidene}methyl)-1-methylpyridinium methylsulfate, 2-{ethyl-4-[(4E)-4-(4-hydroxybenzylidene)-3-methyl-5-oxo-4,5-dihydro-1H-pyrazol-1-yl]anilino}-N,N,N-trimethylethanaminium methylsulfate, 2-[4-((4E)-4-{[4-(dimethylamino)-1-naphthyl]methylene}-3-methyl-5-oxo-4,5-dihydro-1H-pyrazol-1-yl)(ethyl)anilino]-N,N,N-trimethylethanaminium methylsulfate, 2-{ethyl-4-[(4E)-4-(4-methoxybenzylidene)-3-methyl-5-oxo-4,5-dihydro-1H-pyrazol-1-yl]anilino}-N,N,N-trimethyl-ethanaminium methylsulfate and 2-((4E)-4-{(2E)-3-[4-(dimethylamino)phenyl]-2-propen-1-ylidene}-3-methyl-5-oxo-4,5-dihydro-1H-pyrazol-1-yl)-3-methyl-1,3-benzothiazol-3-ium methylsulfate.

Preferred compounds of the general formula (I) are: 2-[((4E)-4-[4-(dimethylamino)benzylidene]-3-methyl-5-oxo-4,5-dihydro-1H-pyrazol-1-yl]-1-methylpyridinium methylsulfate, 2-{(4E)-4-[4-(dimethylamino)benzylidene]-3-methyl-5-oxo-4,5-dihydro-1H-pyrazol-1-yl}-3-methyl-1, 3-benzothiazol-3-ium methylsulfate, 2-[(4E)-4-(4-hydroxybenzylidene)-3-methyl-5-oxo-4,5-dihydro-1H-pyrazol-1-yl]-1-methylpyridinium methylsulfate, 2-[(4E)-4-(4-hydroxybenzylidene)-3-methyl-5-oxo-4,5-dihydro-1H-pyrazol-1-yl]-3-methyl-1,3-benzothiazol-3-ium methylsulfate, 2-[(4E)-4-(4-hydroxy-3-methoxy-benzylidene)-3-methyl-5-oxo-4,5-dihydro-1H-pyrazol-1-yl]-1-methylpyridinium methylsulfate, 2-[(4E)-4-(4-hydroxy-3-methoxybenzylidene)-3-methyl-5-oxo-4,5-dihydro-1H-pyrazol-1-yl]-3-methyl-1,3-benzothiazol-3-ium methylsulfate, 2-((4E)-4-{[4-(dimethylamino)-1-naphthyl]

methylene}-3-methyl-5-oxo-4,5-dihydro-1H-pyrazol-1-yl)-1-methylpyridinium methylsulfate, 2-((4E)-4-{[4-(dimethylamino)-1-naphthyl]methylene}-3-methyl-5-oxo-4,5-dihydro-1H-pyrazol-1-yl)-3-methyl-1,3-benzothiazol-3-ium methylsulfate and 2-((4E)-4-{(2E)-3-[4-(dimethylamino)phenyl]-2-propen-1-ylidene}-3-methyl-5-oxo-4,5-dihydro-1H-pyrazol-1-yl)-3-methyl-1,3-benzothiazol-3-ium methylsulfate.

The dye derivatives of the general formula (I) according to the invention are accessible by customary synthesis methods from commercially available or easy-to-produce components.

By a general process according to L. Knorr (*Liebigs Annalen der Chemie*, 1887, 238, pages 137-219), the pyrazolones substituted by heterocyclic radicals can also be produced by condensation of acetoacetic esters with selected hydrazine compounds. The reaction carried out below with selected aldehydes ultimately produces the described compounds. A general synthesis route is shown in scheme 1.

Scheme 1:

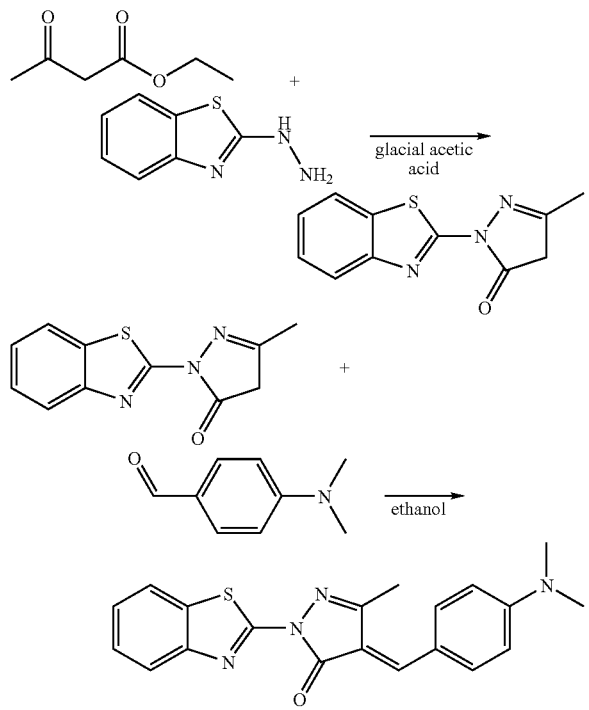

The cationic dye is obtained in the subsequent step according to scheme 2 by quaternization of the heterocyclic nitrogen atoms with alkylating agents of the general formula X—$R_6$, where X is chlorine, bromine, iodine or methylsulfate, $R_6$ is a branched or linear $C_1$-$C_6$-alkyl group, a branched or linear $C_2$-$C_4$-hydroxyalkyl group or a branched or a linear $C_4$-$C_6$-polyhydroxyalkyl group, and Q is any dye radical.

Scheme 2:

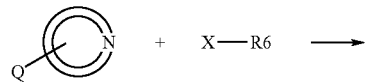

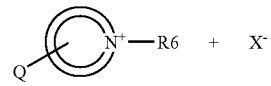

The cationic pyrazolone dyes of the general formula (I) according to the invention permit an even coloring of fiber materials, in particular human hair, with good stability towards light, perspiration and shampooing. The compounds of the general formula (I) according to the invention exhibit an intense, brilliant coloring of keratin fibers, in particular of human hair, but also wool, furs and other fiber materials, under gentle conditions.

The present invention therefore further provides an agent for coloring keratin fibers, in particular human hair, which is characterized in that it comprises at least one cationic pyrazolone dye of the general formula (I).

The cationic pyrazolone dyes of the general formula (I) are present in the coloring agents according to the invention preferably in an amount of from 0.01 to 10 percent by weight, in particular 0.1 to 8 percent by weight.

Besides the cationic pyrazolone dyes of the general formula (I), the coloring agent according to the invention can additionally also comprise further known direct dyes from the group consisting of nitro dyes, azo dyes, anthraquinone dyes and triphenylmethane dyes, such as, for example, 1,4-bis[(2-hydroxyethyl)amino]-2-nitrobenzene, 1-(2-hydroxyethyl)amino-2-nitro-4-[di(2-hydroxyethyl)amino]benzene, (HC Blue No. 2), 1-amino-3-methyl-4-[(2-hydroxyethyl)amino]-6-nitrobenzene, (HC Violet No. 1), 4-[ethyl-(2-hydroxyethyl)amino]-1-[(2-hydroxyethyl)amino]-2-nitrobenzene hydrochloride (HC Blue No. 12), 1-[(2,3-dihydroxypropyl)amino]-4-[methyl-(2-hydroxyethyl)amino]-2-nitrobenzene (HC Blue No. 10), 1-[(2,3-dihydroxypropyl)amino]-4-[ethyl-(2-hydroxy-ethyl)amino]-2-nitrobenzene hydrochloride (HC Blue No. 9), 1-(3-hydroxypropylamino)-4-[di(2-hydroxyethyl)-amino]-2-nitrobenzene, (HC Violet No. 2); 1-amino-4-[(2-hydroxyethyl)amino]-2-nitrobenzene (HC Red No. 7), 2-amino-4,6-dinitrophenol, 1,4-diamino-2-nitrobenzene (CI76070), 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-amino-2-nitro-1-((prop-2-en-1-yl)amino)-benzene, 4-amino-3-nitrophenol, 4-[(2-hydroxyethyl)-amino]-3-nitrophenol, 4-[(2-nitrophenyl)amino]phenol (HC Orange No. 1), 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene, (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)-amino]-4,6-dinitrophenol, 4-ethylamino-3-nitrobenzoic acid, 2-[(4-amino-2-nitrophenyl)amino] benzoic acid, 2-chloro-6-ethylamino-4-nitrophenol, 2-amino-6-chloro-4-nitrophenol, 4-[(3-hydroxypropyl)amino]-3-nitro-phenol, 2,5-diamino-6-nitropyridine, 3-amino-6-(methylamino)-2-nitropyridine, 1,2,3,4-tetrahydro-6-nitroquinoxaline, 7-amino-3,4-dihydro-6-nitro-2H-1,4-benzoxazine (HC Red No. 14), 1,2-diamino-4-nitrobenzene (CI76020), 1-amino-2-[(2-hydroxyethyl)amino]-5-nitrobenzene (HC Yellow No. 5), 1-(2-hydroxyethoxy)-2-[(2-hydroxyethyl)-amino]-5-nitrobenzene, (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-amino-2-methyl-6-nitrobenzene, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride, (HC Yellow No. 9), 1-[(2-ureidoethyl)amino]-4-nitrobenzene, 4-[(2,3-dihydroxypropyl)amino]-3-nitro-1-trifluoromethylbenzene, (HC Yellow No. 6), 1-chloro-2,4-bis[(2-hydroxy-ethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene, (HC Yellow No. 13), 4-[(2-hydroxyethyl)amino]-3-nitrobenzonitrile (HC Yellow No. 14), 4-[(2-hydroxyethyl)amino]-3-nitro-benzamide (HC Yellow No. 15), 2,4-dinitro-1-hydroxy-naphthalene, 1,4-di[(2,3-dihydroxypropyl)amino]-9,10-anthraquinone, 1,4-di[(2-hydroxyethyl)amino]-9,10-anthraquinone (CI61545, Disperse Blue 23), 1-amino-4-hydroxy-9,10-anthraquinone (CI60710, Disperse Red 15), 1-hydroxy-4-[(4-methyl-2-sulfophenyl)amino]-9,10-anthraquinone, 7-beta-D-glucopyranosyl-9,10-dihydro-1-methyl-9,10-dioxo-3,5,6,8-tetrahydroxy-2-anthracenecarboxylic acid (CI75470, Natural Red 4), 1-[(3-aminopropyl)amino]-9,10-anthraquinone (HC Red No. 8), 1,4-diamino-9,10-anthraquinone (CI61100, Disperse Violet No. 1), 1-amino-4-(methylamino)-9,10-anthraquinone (CI61105, Disperse Violet No. 4, Solvent Violet No. 12), N-(6-((3-chloro-4-(methylamino)phenyl)imino)-4-methyl-3-oxo-1,4-cyclohexadien-1-yl)urea (HC Red No. 9), 2-((4-(di(2-hydroxyethyl)-amino)phenyl)amino)-5-((2-hydroxyethyl)amino)-2,5-cyclo-hexadiene-1,4-dione (HC Green No. 1), 2-hydroxy-1,4-naphthoquinone (CI75480, Natural Orange No. 6), 1,2-dihydro-2-(1,3-dihydro-3-oxo-2H-indol-2-ylidene)-3H-indol-3-one (CI73000), 1,3-bis(dicyanomethylene)-indane, di[4-(diethylamino)phenyl][4-(ethylamino)-naphthyl]carbenium chloride (CI42595; Basic Blue No. 7), di[4-(dimethylamino)phenyl][4-(phenylamino)-naphthyl] carbenium chloride (CI44045; Basic Blue No. 26), Basic Blue No. 77, 8-amino-2-bromo-5-hydroxy-4-imino-6-[(3-(trimethylammonio)phenyl)amino]-1(4H)-naphthalinone chloride (CI56059; Basic Blue No. 99), tri(4-amino-3-methylphenyl)carbenium chloride (CI42520; Basic Violet No. 2), di(4-aminophenyl)(4-amino-3-methyl-phenyl)carbenium chloride (CI42510; Basic Violet No. 14), 1-[(4-aminophenyl)azo]-7-(trimethylammonio)-2-naphthol chloride (CI12250; Basic Brown No. 16), 3-[(4-amino-2,5-dimethoxyphenyl)azo]-N,N,N-trimethylbenzenaminium chloride (CI112605, Basic Orange No. 69), 1-[(4-amino-2-nitrophenyl)azo]-7-(trimethylammonio)-2-naphthol chloride (Basic Brown No. 17), 1-[(4-amino-3-nitrophenyl)azo]-7-(trimethylammonio)-2-naphthol chloride (CI12251; Basic Brown No. 17), 2-((4-aminophenyl)azo)-1,3-dimethyl-1H-imidazol-3-ium chloride (Basic Orange No. 31), 3,7-diamino-2,8-dimethyl-5-phenylphenazinium chloride (CI50240; Basic Red No. 2), 1,4-dimethyl-5-[(4-(dimethylamino)phenyl)azo]-1,2,4-triazolium chloride (CI11055; Basic Red No. 22), 1,3-dimethyl-2-((4-dimethylamino)phenyl)azo-1H-imidazol-3-ium chloride (Basic Red No. 51), 2-hydroxy-1-[(2-methoxyphenyl)azo]-7-(trimethylammonio)naphthalene chloride (CI12245; Basic Red No. 76), 3-methyl-1-phenyl-4-[(3-(trimethylammonio)phenyl)azo]pyrazol-5-one chloride (CI12719; Basic Yellow No. 57), 1-methyl-4-((methylphenylhydrazono)methyl)pyridinium methylsulfate (Basic Yellow No. 87), 1-(2-morpholiniumpropylamino)-4-hydroxy-9,10-anthraquinone methylsulfate, 1-[(3-(dimethylpropylaminium)propyl)-amino]-4-(methylamino)-9,10-anthraquinone chloride, 1-[di(2-hydroxyethyl)amino]-3-methyl-4-[(4-nitrophenyl)azo] benzene (CI11210, Disperse Red No. 17), 1-[di(2-hydroxyethyl)amino]-4-[(4-nitrophenyl)azo]benzene, (Disperse Black No. 9), 4-[(4-aminophenyl)azo]-1-[di(2-hydroxyethyl)amino]-3-methylbenzene, (HC Yellow No. 7) or 2,6-diamino-3-[(pyridin-3-yl)azo]pyridine or 2-((4-(ethyl (2-hydroxyethyl)amino)-2-methylphenyl)azo)-5-nitro-1,3-thiazole (CI111935; Disperse Blue No. 106), alone or in a mixture with one another.

The coloring agent according to the invention can also comprise all additives which are customary and known for such preparations, for example perfume oils, complexing agents, waxes, preservatives, thickeners, alginates, guar gum, haircare substances, such as, for example, cationic polymers or lanolin derivatives, or anionic, nonionic, amphoteric or cationic surface-active substances. Preference is given to using amphoteric or nonionic surface-active substances, for example betaine surfactants, propionates and glycinates, such as, for example, cocoamphoglycinates or cocoamphodiglycinates, ethoxylated surfactants with 1 to 1000 ethylene oxide units, preferably with 1 to 300 ethylene oxide units, such as, for example, glyceride alkoxylates, for example castor oil ethoxylated with 25 ethylene oxide units, polyglycolamides, ethoxylated alcohols and ethoxylated fatty alcohols (fatty alcohol alkoxylates) and ethoxylated fatty acid sugar esters, in particular ethoxylated sorbitan fatty acid esters. The above-mentioned constituents are used in the amounts customary for such purposes, for example the surface-active substances in a concentration of from 0.1 to 30 percent by weight, and the care substances in an amount of from 0.1 to 5 percent by weight.

The coloring agent according to the invention can, particularly if it is a hair-coloring agent, be in the form of an aqueous or aqueous-alcoholic solution, a cream, a gel, an emulsion or an aerosol foam, where the hair-coloring agent can be formulated either in the form of a single-component preparation, or in the form of a multicomponent preparation, for example in the form of a two-component preparation in which the respective dye derivative of the general formula (I) is packaged separately from the other constituents and the ready-to-use hair-coloring agent is only prepared directly prior to use by mixing the two components.

The coloring agent according to the invention has a pH of from about 2 to about 10, preferably from 5 to 10, and in particular a neutral to basic pH from 7 to 9. To establish the pH according to the invention, either organic or inorganic acids or bases are suitable.

Suitable acids to be mentioned are, in particular, the following acids: α-hydroxycarboxylic acids, such as, for example, glycolic acid, lactic acid, tartaric acid, citric acid or malic acid, ascorbic acid, gluconolactone, acetic acid, hydrochloric acid or phosphoric acid, and mixtures of these acids. Suitable bases are, in particular, sodium carbonate, sodium hydrogencarbonate, alkanolamines, for example mono-ethanolamine or triethanolamine, ammonia, aminomethyl-propanol and sodium hydroxide.

The coloring agent according to the invention is generally used by applying to the hair an amount of the hair-coloring agent sufficient for coloring the hair, about 30 to 120 grams depending on the length of the hair, the hair-coloring agent is left to act at about 15 to 45 degrees Celsius for about 1 to 60 minutes, preferably 5 to 30 minutes, the hair is then thoroughly rinsed with water, optionally washed with a shampoo and finally dried.

The coloring agent described above can also comprise natural or synthetic polymers or modified polymers of natural origin customary for cosmetic compositions, as a result of which setting of the hair is achieved at the same time as the coloring. Such agents are generally referred to as setting tints or setting colors.

Of the synthetic polymers known for this purpose in cosmetics, mention may be made, for example, of polyvinylpyrrolidone, polyvinyl acetate, polyvinyl alcohol or polyacrylic compounds, such as polyacrylic acid or polymethacrylic acid, basic polymers of esters of polyacrylic acid, polymethylacrylic acid and amino alcohols, for example salts or quaternization products thereof, polyacrylonitrile, polyvinyl acetates and copolymers of such compounds, such as, for example, polyvinylpyrrolidone-vinyl acetate; whereas natural polymers or modified natural polymers which may be used are, for example, chitosan (deacetylated chitin) or chitosan derivatives.

The abovementioned polymers may be present in the coloring agent according to the invention in the amounts customary for such agents, in particular in an amount of from about 1 to 5 percent by weight. The pH of the setting tint or setting color according to the invention is preferably about 7 to 9.

The hair-coloring agent with additional setting is used in a known and customary manner by wetting the hair with the setting agent, setting (arranging) the hair in the hair style and then drying it.

The coloring agent according to the invention permits an even, intense and permanent coloring of keratin fibers (for example human hair, wool or furs) without appreciable staining of the skin or scalp, which withstands five and more hair washes without notable fading of the hair color.

The examples below are intended to illustrate the subject matter of the invention in more detail without limiting it thereto.

EXAMPLES

Example 1

Synthesis of 2-(1,3-benzothiazol-2-yl)-5-methyl-2,4-dihydro-3H-pyrazol-3-one 2 g (12.1 mmol) of 2-hydrazino-1,3-benzothiazole and 1.58 g (12.1 mmol) of acetoacetic ester are stirred in 40 ml of glacial acetic acid for 2 hours at 90° C. The mixture is then diluted with water and the precipitated crystals are filtered off with suction, washed again with water and dried under reduced pressure.

Yield: 2.49 g (89% of theory), pale yellow needles $^1$H NMR (CDCl$_3$/300 MHz): δ=2.16 (s, 3H, methyl), 3.50 (s, 2H, methylene, tautomer a), 5.40 (s, 1H, tautomer b), 7.19-7.24 (q, J=16.5 Hz, 2H, tautomer a/tautomer b), 7.39-7.44 (q, J=14.4 Hz, 2H, tautomer a/tautomer b), 7.72-7.75 (t, J=7.5 Hz, 3H, tautomer a/tautomer b), 7.86-7.94 (d, J=16 Hz, 1H, tautomer b).

Example 2

Synthesis of 5-methyl-2-(2-pyridinyl)-2,4-dihydro-3H-pyrazol-3-one 0.5 g (4.44 mmol) of 2-hydrazinopyridine and 0.58 g (4.44 mmol) of acetoacetic ester are stirred in 15 ml of glacial acetic acid for 2 hours at 90° C. The mixture is then diluted with water and the precipitated crystals are filtered off with suction, washed again with water and dried under reduced pressure.

Yield: 0.64 g (82% of theory), colorless crystals $^1$H NMR (CDCl$_3$/300 MHz): δ=2.31 (s, 3H, methyl), 5.45 (s, 1H), 7.13-7.17 (m, 1H, pyridyl), 7.84-7.91 (m, 1H, pyridyl), 7.96-7.98 (m, 1H, pyridyl), 8.22-8.27 (m, 1H, pyridyl).

Example 3

Synthesis of 2-((4E)-4-{[4-(dimethylamino)-phenyl]methylidene}-3-methyl-5-oxo-4,5-dihydro-1H-pyrazol-1-yl)-3-methyl-1,3-benzothiazol-3-ium methylsulfate Stage 1: Synthesis of (4E)-2-(1,3-benzothiazol-2-yl)-4-{[4-(dimethylamino)phenyl]-methylidene}-5-methyl-2,4-dihydro-3H-pyrazol-3-one 1 g (4.32 mmol) of 2-(1,3-benzothiazol-2-yl)-5-methyl-2,4-dihydro-3H-pyrazol-3-one and 1.93 g (12.96 mmol) of 4-(dimethylamino)benzaldehyde are stirred under reflux with the addition of 3 ml of piperidine in absolute ethanol for 2 hours. The mixture is then diluted with water and the bright red precipitate is filtered off, then washed with water and a small amount of cold methanol and dried under reduced pressure.

Yield: 1.4 g (89% of theory), bright red powder $^1$H NMR (CDCl$_3$/300 MHz): δ=2.46 (s, 3H, methyl), 3.16 (s, 6H, dimethyl), 6.76-6.79 (d, J=9.3 Hz, 2H, phenyl), 7.30-7.35 (t, J=16.2, Hz, 1H), 7.39 (s, 1H, olefin), 7.43-7.49 (t, J=16.5 Hz, 1H), 7.84-7.87 (d, J=7.8 Hz, 1H), 8.04-8.06 (d, J=8.1 Hz, 1H), 8.57-8.59 (d, J=8.7 Hz, 2H, phenyl).

Stage 2: Synthesis of 2-((4E)-4-{[4-(dimethylamino)-phenyl]methylidene}-3-methyl-5-oxo-4,5-dihydro-1H-pyrazol-1-yl)-3-methyl-1,3-benzothiazol-3-ium methylsulfate In 60 ml of acetone, 0.82 g (2.26 mmol) of (4E)-2-(1,3-benzothiazol-2-yl)-4-{[4-(dimethylamino)phenyl]-methylidene}-5-methyl-2,4-dihydro-3H-pyrazol-3-one and 1.42 g (11.3 mmol) of dimethyl sulfate are stirred under reflux for 1 hour. The precipitated product is filtered off with suction, washed with acetone and dried under reduced pressure.

Yield: 0.85 g (77% of theory), red powder UV/Vis (DMSO): $\lambda_{max}$=sh 372, 510 nm

Example 4

Synthesis of 2-((4E)-4-{[4-hydroxy-3-(methyloxy)phenyl]methylidene}-3-methyl-5-oxo-4,5-dihydro-1H-pyrazol-1-yl)-3-methyl-1,3-benzothiazol-3-ium methylsulfate Stage 1: Synthesis of (4E)-2-(1,3-benzothiazol-2-yl)-4-{[4-hydroxy-3-(methyloxy)phenyl]-methylidene}-5-methyl-2,4-dihydro-3H-pyrazol-3-one 1 g (4.32 mmol) of 2-(1,3-benzothiazol-2-yl)-5-methyl-2,4-dihydro-3H-pyrazol-3-one and 1.97 g (12.96 mmol) of 4-hydroxy-3-methoxybenzaldehyde are stirred under reflux with the addition of 3 ml of piperidine in absolute ethanol for 2 hours. The mixture is then diluted with water and the orange-yellow precipitate is filtered off, then washed with water and a small amount of cold methanol and dried under reduced pressure.

Yield: 1.07 g (68% of theory), orange-yellow powder $^1$H NMR (d$_6$-DMSO/300 MHz): δ=2.40 (s, 3H, methyl), 3.84 (s, 3H, methoxy), 6.97-7.00 (d, J=8.4 Hz, 1H), 7.33-7.38 (t, J=16.2 Hz, 1H), 7.46-7.51 (t, J=16.5 Hz, 1H), 7.85-7.87 (d, J=7.5 Hz, 2H, phenyl), 8.02-8.04 (d, J=5.7 Hz, 1H), 8.06 (s, 1H, olefin), 8.76 (s, 1H, phenyl).

Stage 2: Synthesis of 2-((4E)-4-{[4-hydroxy-3-(methyloxy)phenyl]methylidene}-3-methyl-5-oxo-4,5-dihydro-1H-pyrazol-1-yl)-3-methyl-1,3-benzothiazol-3-ium methyl-sulfate In 40 ml of acetone, 0.50 g (1.37 mmol) of (4E)-2-(1,3-benzothiazol-2-yl)-4-{[4-hydroxy-3-(methyloxy)-phenyl]methylidene}-5-methyl-2,4-dihydro-3H-pyrazol-3-one and 0.86 g (6.85 mmol) of dimethyl sulfate are stirred under reflux for one hour. The precipitated product is filtered off with suction, washed with acetone and dried under reduced pressure.

Yield: 0.52 g (77% of theory), orange-colored powder UV/Vis (DMSO): $\lambda_{max}$=412, 572 nm Example 5

Synthesis of 2-{(4E)-4-[4-(dimethylamino)-benzylidene]-3-methyl-5-oxo-4,5-dihydro-1H-pyrazol-1-yl}-1-methylpyridinium methyl-sulfate Stage 1: Synthesis of (4E)-4-[4-(dimethylamino)-benzylidene]-5-methyl-2-(2-pyridinyl)-2,4-dihydro-3H-pyrazol-3-one 1.3 g (7.42 mmol) of 5-methyl-2-(2-pyridinyl)-2,4-dihydro-3H-pyrazol-3-one and 1.68 g (11.13 mmol) of 4-(dimethylamino)benzaldehyde are stirred under reflux with the addition of 3 ml of piperidine in absolute ethanol for 2 hours. The mixture is then diluted with water and the orange-red precipitate is filtered off, then washed with water and dried under reduced pressure.

Yield: 1.25 g (55% of theory), orange-red powder $^1$H NMR (CDCl$_3$/300 MHz): δ=2.40 (s, 3H, methyl), 3.13 (s, 6H, dimethyl), 6.74 (d, 2H, J=9.3 Hz, phenyl), 7.08-7.12 (t, 1H, pyridyl), 7.31 (s, 1H, olefin), 7.73-7.79 (t, 1H, pyridyl), 8.24-8.27 (d, 1H, pyridyl), 8.54-8.56 (d, 1H, pyridyl), 8.58 (d, 2H, J=9.3 Hz, phenyl).

Stage 2: Synthesis of 2-{(4E)-4-[4-(dimethylamino)-benzylidene]-3-methyl-5-oxo-4,5-dihydro-1H-pyrazol-1-yl}-1-methylpyridinium methyl-sulfate In 40 ml of acetone, 0.4 g (1.3 mmol) of (4E)-4-[4-(dimethylamino)benzylidene]-5-methyl-2-(2-pyridinyl)-2,4-dihydro-3H-pyrazol-3-one and 1.66 g (13.06 mmol) of dimethyl sulfate are stirred under reflux for one hour. The precipitated product is filtered off with suction, washed with acetone and dried under reduced pressure.

Yield: 0.40 g (72% of theory), orange-red powder $^1$H NMR (D$_2$O/300 MHz): δ=2.15 (s, 3H, methyl), 3.04 (s, 6H, dimethyl), 4.28 (s, 3H, methyl), 6.48 (d, 2H, J=9.0 Hz, phenyl), 7.44 (s, 1H, olefin), 7.85-7.90 (m, 2H, pyridyl), 8.22 (d, 2H, J=9.0 Hz, phenyl), 8.47-8.53 (t, 1H, pyridyl), 8.74-8.76 (d, 1H, pyridyl).

Example 6

Synthesis of 2-[(4E)-4-(4-hydroxy-3-methyl-oxybenzylidene)-3-methyl-5-oxo-4,5-dihydro-1H-pyrazol-1-yl]-1-methylpyridinium methylsulfate Stage 1: Synthesis of (4E)-4-[4-hydroxy-3-methyloxy-benzylidene)-5-methyl-2-(2-pyridinyl)-2,4-dihydro-3H-pyrazol-3-one 1.4 g (7.99 mmol) of 5-methyl-2-(2-pyridinyl)-2,4-dihydro-3H-pyrazol-3-one and 1.84 g (11.98 mmol) of 4-hydroxy-3-methoxybenzaldehyde are stirred under reflux with the addition of 3 ml of piperidine in absolute ethanol for 2 hours. The mixture is then diluted with water and slowly rendered neutral with 2N hydrochloric acid. After cooling in the ice bath, the orange precipitate which settles out is filtered off, washed with water and dried under reduced pressure.

Yield: 1.12 g (45% of theory), dark yellow powder m.p.: 153° C.

Stage 2: Synthesis of 2-[(4E)-4-(4-hydroxy-3-methyl-oxybenzylidene)-3-methyl-5-oxo-4,5-dihydro-1H-pyrazol-1-yl]-1-methylpyridinium methylsulfate In 45 ml of dry tetrahydrofuran, 0.4 g (1.29 mmol) of (4E)-4-[4-hydroxy-3-methyloxybenzylidene]-5-methyl-2-(2-pyridinyl)-2,4-dihydro-3H-pyrazol-3-one and 1.65 g (12.93 mmol) of dimethyl sulfate are stirred under reflux for one hour. The precipitated product is filtered off with suction, washed with tetrahydrofuran and dried under reduced pressure.

Yield: 0.45 g (80% of theory), orange powder $^1$H NMR (D$_2$O/300 MHz): δ=2.09 (s, 3H, methyl), 3.68 (s, 3H, methyl), 4.18 (s, 3H, —O-methyl), 7.23 (s, 1H, olefin), 7.33-7.35 (m, 1H, pyridyl), 7.88-7.95 (t, 1H, pyridyl), 8.22 (s, 1H, phenyl-OH), 8.50-8.55 (t, 1H, pyridyl), 8.75-8.77 (m, 1H, pyridyl).

Example 7

Synthesis of 2-((4E)-4-{(2E)-3-[4-(dimethylamino)phenyl]-2-propen-1-ylidene}-3-methyl-5-oxo-4,5-dihydro-1H-pyrazol-1-yl)-3-methyl-1,3-benzothiazol-3-ium methylsulfate Stage 1: Synthesis of (4E)-2-(1,3-benzothiazol-2-yl)-4-{(2E)-3-[4-(dimethylamino)phenyl]-2-propen-1-ylidene}-5-methyl-2,4-dihydro-3H-pyrazol-3-one 1 g (4.32 mmol) of 2-(1,3-benzothiazol-2-yl)-5-methyl-2,4-dihydro-3H-pyrazol-3-one and 1.51 g (8.64 mmol) of 4-N,N-dimethylaminocinnamaldehyde are stirred under reflux with the addition of 3 ml of piperidine in absolute ethanol for 2 hours. The mixture is then diluted with water and the dark red precipitate is filtered off, then washed with water and a small amount of cold methanol and dried under reduced pressure.

Yield: 1.44 g (86% of theory), dark red powder m.p.: 134° C.

Stage 2: Synthesis of 2-((4E)-4-{(2E)-3-[4-(dimethylamino)phenyl]-2-propen-1-ylidene}-3-methyl-5-oxo-4,5-dihydro-1H-pyrazol-1-yl)-3-methyl-1,3-benzothiazol-3-ium methylsulfate In 40 ml of acetone, 1.30 g (3.35 mmol) of (4E)-2-(1,3-benzothiazol-2-yl)-4-{(2E)-3-[4-(dimethylamino)-phenyl]-2-propen-1-ylidene}-5-methyl-2,4-dihydro-3H-pyrazol-3-one and 2.11 g (16.75 mmol) of dimethyl sulfate are stirred under reflux for 1 hour. The precipitated product is filtered off with suction, washed with acetone and dried under reduced pressure.

Yield: 1.13 g (65% of theory), brown-red powder UV/Vis (DMSO): $\lambda_{max}$=372, 482, 570 nm Examples 8 to 12

Coloring Agents 2.5 mmol dye of the general formula (I)
5.0 g ethanol
4.0 g decylpolyglucose
0.2 g ethylenediaminotetraacetic acid disodium salt hydrate ad 100.0 g water, completely demineralized The above coloring agent is adjusted to a pH of from 6 to 7. Hair coloring takes place by applying to the hair an amount of the coloring agent sufficient for the hair coloring, rinsing the hair with lukewarm water after a contact time of 30 minutes at 40° C. and then drying it. The coloring results are summarized in table 1 below.

TABLE 1

| Example No. | Dye of the formula (I) according to example (No.) | Color result |
| --- | --- | --- |
| 8 | 2-((4E)-4-{[4-(dimethylamino)-phenyl]methylidene}-3-methyl-5-oxo-4,5-dihydro-1H-pyrazol-1-yl)-3-methyl-1,3-benzothiazol-3-ium methylsulfate (3) | intense bright red |
| 9 | 2-((4E)-4-{[4-hydroxy-3-(methyloxy)-phenyl]methylidene}-3-methyl-5-oxo-4,5-dihydro-1H-pyrazol-1-yl)-3-methyl-1,3-benzothiazol-3-ium methylsulfate (4) | orange-brown |
| 10 | 2-{(4E)-4-[4-(dimethylamino)-benzylidene]-3-methyl-5-oxo-4,5-dihydro-1H-pyrazol-1-yl}-1-methylpyridinium methylsulfate (5) | orange-red |
| 11 | 2-[(4E)-4-(4-hydroxy-3-methyloxy-benzylidene)-3-methyl-5-oxo-4,5-dihydro-1H-pyrazol-1-yl]-1-methylpyridinium methylsulfate (6) | gold-orange |
| 12 | 2-((4E)-4-{(2E)-3-[4-(dimethyl-amino)phenyl]-2-propen-1-ylidene}-3-methyl-5-oxo-4,5-dihydro-1H-pyrazol-1-yl)-3-methyl-1,3-benzo-thiazol-3-ium methylsulfate (7) | red-brown |

Unless stated otherwise, all of the percentages are percentages by weight.

The invention claimed is:

1. An agent for coloring keratin fibers comprising from 0.01 to 10% by weight of a cationic pyrazolone dye of the general formula (I),

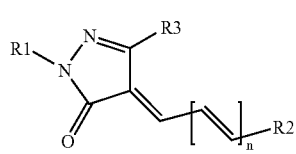

(I)

in which
n is 0 or 1;
$R_1$ and $R_2$, independently of one another, are one of the formulae (II), (III), (IV), (V) or (VI),

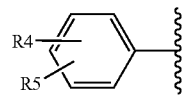
(II)

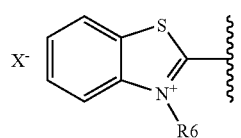
(III)

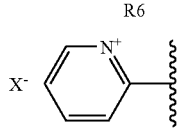
(IV)

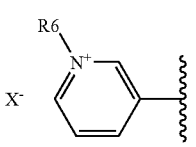
(V)

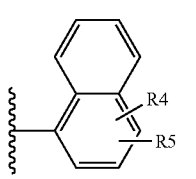
(VI)

$R_3$ is a $C_1$-$C_6$-alkyl group, a $C_1$-$C_6$-alkylcyano group, a hydroxyl group, a methoxymethyl group, a $C_1$-$C_6$-N,N-dialkylamino group, a carboxamide group, a $C_1$-$C_6$-alkylsulfonic acid group, a sulfonic acid group, a sulfonic acid ester group, a carboxylic acid group, a carboxylic acid ester group, an amino group, a sulfonamide group, a methyl group, an isopropyl group, a tert-butyl group or a phenyl group;

$R_4$ is a hydrogen atom, a $C_1$-$C_6$-alkylamino group, a $C_1$-$C_6$-N,N-dialkylamino group, a $C_1$-$C_6$-alkylcyano group, a hydroxyl group, a nitro group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylsulfonic acid group, a $C_1$-$C_6$-alkylsulfonic acid ester group, or an —N-(L)-(L)-B$^+$ group;

$R_5$ is a hydrogen atom, a $C_1$-$C_6$-alkylamino group, a $C_1$-$C_6$-N, N-dialkylamino group, a $C_1$-$C_6$-alkylcyano group, a hydroxyl group, a nitro group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylsulfonic acid group, a $C_1$-$C_6$-alkylsulfonic acid ester group, an —N-(L)-(L)-B$^+$ group or a radical of the formulae (VII), (VIII) or (IX);

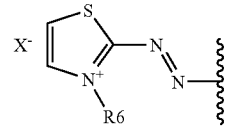
(VII)

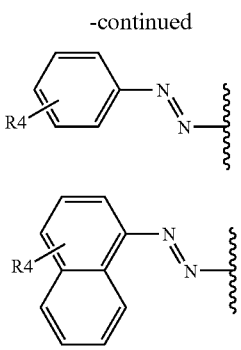

R6 is a branched or linear $C_1$-$C_6$-alkyl group, a branched or linear $C_2$-$C_4$-hydroxyalkyl group or a branched or a linear $C_4$-$C_6$-polyhydroxyalkyl group;

L is a $C_1$-$C_6$-alkylene group;

$B^+$ is the following radical groups:

a) an aromatic, heterocyclic quaternary ammonium compound, preferably a quaternary compound of N-methylimidazole, a quaternary compound of N-allylimidazole, a quaternary compound of 2-ethylimidazole, a quaternary compound of 1,2-dimethylimidazole, a quaternary compound of pyridine, a quaternary compound of 4-dimethylaminopyridine, a quaternary compound of pyrimidine, a quaternary compound of pyrazole, a quaternary compound of N-methylpyrazole or a quaternary compound of quinoline; or b) a nonaromatic heterocyclic quaternary ammonium compound, in particular a quaternary compound of N-methylmorpholine, a quaternary compound of N-ethylmorpholine or a quaternary compound of 1-methylpiperidine; or c) a quaternary alkylammonium compound or arylammonium compound of the formula $NR_aR_bR_c$, where $R_a$, $R_b$ and $R_c$, independently of one another, are a henzyl radical, a phenyl radical or a $C_1$- to $C_6$-alkyl radical, in particular a methyl radical, an ethyl radical, a propyl radical, an isopropyl radical or a butyl radical, where the abovementioned alkyl radicals may be unsubstituted or substituted by one or more hydroxyl groups or amino groups; or d) a quaternary phosphonium group, for example a tributylphosphonium group, but in particular a trimethylammonium group or a triethylammonium group; and $X^-$ is an anion;

with the proviso that at least one of the radicals $R_1$ and $R_2$ is a cationic group.

2. The agent as claimed in claim 1, wherein the cationic pyrazolone dye of the general formula (I) is selected from the group consisting of 2-{(4E)-4-[4-(dimethylamino)benzylidene]-3-methyl-5-oxo-4,5-dihydro-1H-pyrazol-1-yl}-1-methylpyridinium methylsulfate, 2-{(4E)-4-4-(dinethylamino)henzylidene]-3-methyl-5-oxo-4,5-dihydro-1H-pyrazol-1-yl}-3-methyl-1,3-henzothiazol-3-ium methylsulfate, 2-[(4E)-4-(4-hydroxybenzylidene)-3-methyl-5-oxo-4,5-dihydro-1H-pyrazol-1-yl-1-methylpyridinium methylsulfate, 2-(4R)-4-(4-hydroxybenzylidene)-3-mothyl-5-oxo-4,5-dihydro-1H-pyrazol-1-yl]-3-methyl-1,3-benzothiazol-3-ium methylsulfate, 2-[(4E)-4- (4-hydroxy-3-methoxybenzylidene)-3-methyl-5-oxo-4,5-dihydro-1H-pyrazol-1-yl]-1-methylpyridinium nethylsulfate, 2-[(4E)-4-(4-hydroxy-3-methoxybenzyiidene)-3-methyl-5-oxo-4,5-dihydro-1H-pyrazol-1-yl]-3-methyl-1,3-henzothiazoi-3-ium methylsultate, 2-((4E)-4-{[4-(dimethylamino)-1-naphthyl]methylene}-3-methyl-5-oxo-4,5-dihydro-1H-pyrazol-1-yl)-1-methylpyridiniun methyl-sulfate, 2-((4E)-4-{[4-(dimethylamino)-1-naphthyl]methylene}-3-methyl-5-oxo-4,5-dihydro-1H-pyrazol-1-yl)-3-methyl-1,3-benzothiazol-3-ium methylsulfate and 2-((4E)-4-{(2E)-3-[4-(dimethylamino)phenyl]-2-propen-1-ylidene}-3-methyl-5-oxo-4,5-dihydro-1H-pyrazol-1-yl)-3-methyl-1,3-benzothiazol-3-ium methylsulfate.

3. The agent as claimed in claim 1, and further comprising at least one further direct dye selected from the group consisting of nitro dyes, azo dyes, anthraquinone dyes and triphenylmethane dyes.

4. The agent as claimed in claim 1, and further comprising at least one natural or synthetic polymer customary for cosmetic agents and/or at least one modified polymer of natural origin.

5. The agent as claimed in claim 1, wherein the agent has a pH of from 7 to 9.

6. The agent as claimed in claim 1, wherein the agent is a hair-coloring agent.

7. A method for dyeing hair comprising:
applying to the hair, an amount of a hair colorant comprising at least one cationic pyrazolone dye of general formula (I) sufficient for dyeing the hair;
leaving the hair colorant to act on the hair at a temperature from 15 to 50° C. for 1 to 60 minutes;
rinsing the hair with water; and
drying the hair

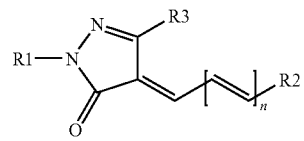

in which
n is 0 or 1;
$R_1$ and $R_2$, independently of one another, are one of the formulae (II), (III), (IV), (V) or (VI),

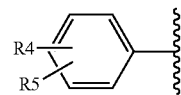

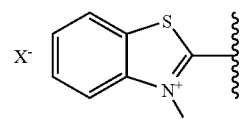

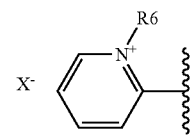

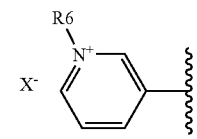

-continued (VI)

[structure with R4, R5 on naphthalene]

$R_3$ is a $C_1$-$C_6$-alkyl group, a $C_1$-$C_6$-alkylcyano group, a hydroxyl group, a methoxymethyl group, a $C_1$-$C_6$-N,N-dialkylamino group, a carboxamide group, a $C_1$-$C_6$-alkylsulfonic acid group, a sulfonic acid group, a sulfonic acid ester group, a carboxylic acid group, a carboxylic acid ester group, an amino group, a sulfonamide group, a methyl group, an isopropyl group, a tert-butyl group or a phenyl group;

$R_4$ is a hydrogen atom, a $C_1$-$C_6$-alkylamino group, a $C_1$-$C_6$-N,N-dialkylamino group, a $C_1$-$C_6$-alkylcyano group, a hydroxyl group, a nitro group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxyhic acid group, a $C_1$-$C_6$-alkylcarboxylic acid ester group, a $C_1$-$C_6$-alkylsulfonic acid group, a $C_1$-$C_6$-alkylsulfonic acid ester group, or an —N-(L)-(L)-B$^+$ group;

$R_5$ is a hydrogen atom, a $C_1$-$C_6$-alkylamino group, a $C_1$-$C_6$-N,N-dialkylamino group, a $C_1$-$C_6$-alkylcyano group, a hydroxyl group, a nitro group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylsulfonic acid group, a $C_1$-$C_6$-alkylsulfonic acid ester group, an —N-(L)-(L)-B$^+$ group or a radical of the formulae (VII), (VIII) or (IX);

(VII)

(VIII)

(IX)

$R_6$ is a branched or linear $C_1$-$C_6$-alkyl group, a branched or linear $C_2$-$C_4$-hydroxyalkyl group or a branched or a linear $C_4$-$C_6$-polyhydroxyalkyl group;

L is a $C_1$-$C_6$-alkylene group;

B$^+$ is the following radical groups:

a) an aromatic, heterocyclic quaternary anmonium compound, preferably a quaternary compound of N-methylimidazole, a quaternary compound of N-allylimidazole, a quaternary compound of 2-ethylimidazole, a quaternary compound of 1,2-dimethylimidazole, a quaternary compound of pyridine, a quaternary compound of 4-dimethylaminopyridine, a quaternary compound of pyrimidine, a quaternary compound of pyrazole, a quaternary compound of N-methylpyrazole or a guaternary compound of quinoline; or b) a nonaromatic heterocyclic quaternary ammonium compound, in particular a quaternary compound of N-methylmorpholine, a quaternary compound of N-ethylmorpholine or a quaternary compound of 1-methylpiperidine; or c) a quaternary alkylammonium compound or arylammonium compound of the formula NR$_a$R$_b$R$_C$, where R$_a$, R$_b$ and R$_C$, independently of one another, are a benzyl radical, a phenyl radical or a $C_1$- to $C_6$-alkyl radical, in particular a methyl radical, an ethyl radical, a propyl radical, an isopropyl radical or a butyl radical, where the abovementioned alkyl radicals may be unsubstituted or substituted by one or more hydroxyl groups or amino groups; or d) a quaternary phosphonium group, for example a tributylphosphonium group, but in particular a trimethylammonium group or a triethylammonium group; and X$^-$ is an anion;

with the proviso that at least one of the radicals $R_1$ and $R_2$ is a cetionic group.

8. The method as claimed in claim 7, wherein the cationic pyrazolone dye of general formula (I) is selected from the group consisting of 2{(4E)-4-[4-(dimethylamino)benzylidene]-3-methyl-3-oxo-4,5-dihydro-1H-pyrazol-1-yl}-1-methylpyridinium methyl-sulfate, 2-{(4E)-4-[4-(dimethylamino)benzylidene]-3-methyl-5-oxo-4,5-dihydro-1H-pyrazol-1-yl}-3-methyl-1,3-benzothiazol-3-ium methylsulfate, 2-[(4E)-4-(4-hydroxybenzylidene)-3-methyl-5-oxo-4,5-dihydro-1H-pyrazol-1-yl]-1-methylpyridinium methylsulfate, 2-[(4E)-4-(4-hydroxybenzylidene)-3-methyl-5-oxo-4,5-dihydro-1H-pyrazol-1-yl]-3-methyl-1,3-benzothiazol-3-ium methylsulfate, 2-[(4E)-4-(4-hydroxy-3-methoxyhenzylidene) 3-methyl-5-oxo-4,5-dihydro-1H-pyrazol-1-yl]-1-methylpyridinium methylsulfate, 2-[(4E)-4-(4-hydroxy-3-methoxybenzylidene) -3-methyl-5-oxo-4,5-dihydro-1H-pyrazol-1-yl]-3-methyl-1, 3-benzo-thiazol-3-ium methylsulfate, 2-((4E)-4-{[4-(dimethylamino)-1-naphthyl]methylene}-3-methyl-5-oxo-4,5-dihydro-1H-pyrazo-1-yl) -1-methylpyridinium methylsulfate, 2-((4E)-4-[4-(dimethylamino)-1-naphthyl]methylene}-3-methyl-5-oxo-4,5-dihydro-1H-pyrazol-1-yl)-3-methyl-1,3-benzothiazol-3-ium methylsulfate and 2-((4E)-4-{(2E)-3-[4-(dimethylamino)phenyl]-2-propen-1-ylidene}-3-methyl-5-oxo-4,5-dihydro-1H-pyrazol-1-yl)-3-methyl-1,3-henzothiazol-3-ium metyhylsulfate.

9. The method as claims in claim 7, wherein the hair is washed with a shampoo before drying.

10. A method for the simultaneous dyeing and setting hair comprising:

wetting the hair with am agent comprising (a) at least one natural polymer or synthetic polymer or modified polymer of natural origin customary for cosmetic agents and (b) at least one cationic pyrazolone dye of general formula (I);

styling the hair; and drying the hair

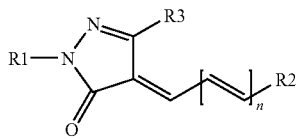
(I)

in which n is 0 or 1;

R₁ and R₂, independently of one another, are one of the formulae (II), (III), (IV), (V), or (VI),

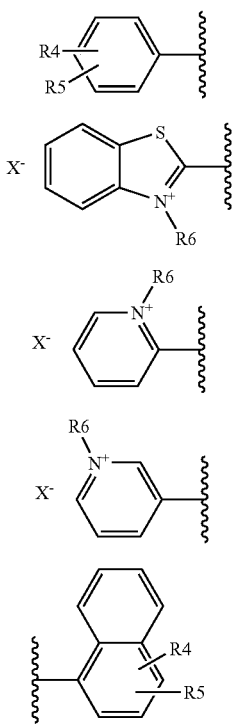

$R_3$ is a $C_1$-$C_6$-alkyl group, a $C_1$-$C_6$-alkylcyano group, a hydroxyl group, a methoxymethyl group, a $C_1$-$C_6$-N,N-dialkylamimo group, a carboxamide group, a $C_1$-$C_6$-alkylsulfonic acid group, a sulfonic acid group, a sulfonic acid ester group, a carboxylic acid group, a carboxylic acid ester group, an amino group, a sulfonamide group, a methyl group, an isopropyl group, a tert-butyl group or a phenyl group;

$R_4$ is a hydrogen atom, a $C_1$-$C_6$-alkylamino group, a $C_1$-$C_6$-N,N-dialkylamino group, a $C_1$-$C_6$-alkylcyano group, a hydroxyl group, a nitro group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylsulfonic acid group, a $C_1$-$C_6$-alkylsulfonic acid ester group, or an —N-(L)-(L)-B⁺ group;

$R_5$ is a hydrogen atom, a $C_1$-$C_6$-alkylamino group, a $C_1$-$C_6$-N,N-dialkylamino group, a $C_1$-$C_6$-alkylcyano group, a hydroxyl group, a nitro group, a methoxymethyl group, a tert-butyl group, an isopropyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylsulfonic acid group, a $C_1$-$C_6$-alkylsulfonic acid ester group, an —N-(L)-(L)-B⁺ group or a radical of the formulae (VII), (VIII) or (IX);

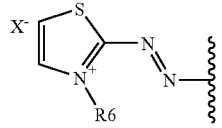
(VII)

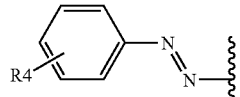
(VIII)

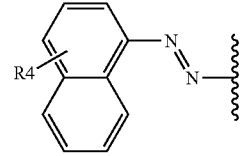
(IX)

$R_6$ is a branched or linear $C_1$-$C_6$-alkyl group, a branched or linear $C_2$-$C_4$-hydroxyalkyl group or a branched or a linear $C_4$-$C_6$-polyhydroxyalkyl group;

L is a $C_1$-$C_6$-alkylene group;

B⁺ is the following radical groups:

a) an aromatic, heterocyclic quaternary ammonium compound, preferably a quaternary compound of N-methylimidazole, a quaternary compound of N-allylimidazole, a quaternary compound of 2-ethylimidazole, a quaternary compound of 1,2-dimethylimidazole, a quaternary compound of pyridine, a quatermary compound of 4-dimethylaminopyridine, a quaternary compound of pyrimidine, a quaternary compound of pyrazole, a quaternary compound of N-methylpyrazole or a quaternary compound of quinoline; or b) a nonaromatic heterocyclic guaternary ammonium compound, in particular a quaternary compound of N-methylmorpholine, a quaternary compound of N-ethylmorpholine or a quaternary compound of 1-methylpiperidine; or c) a quaternary alkylammonium compound or arylammonium compound of the formula $NR_aR_bR_c$, where $R_a$, $R_b$ and $R_c$, independently of one another, are a bensyl radical, a phenyl radical or a $C_1$- to $C_6$-alkyl radical, in particular a methyl radical, an ethyl radical, a propyl radical, an isopropyl radical or a butyl radical, where the abovementioned alkyl radicals may be unsubstituted or substituted by one or more hydroxyl groups or amino groups; or d) a quaternary phosphonium group, for example a tributylpbosphonium group, but in particular a trimethylammonium group or a triethylammonium group; and X⁻ is an anion;

with the proviso that at least one of the radicals $R_1$ and $R_2$ is a cationic group.

11. The method as claimed in claim 10, wherein the cationic pyrazolone dye of general formula (I) is selected from the group consisting of 2-{(4E)-4-[4-(dimethylamino) benzylidene]-3-methyl-5-oxo-4,5-dihydro-1H-pyrazol -1-yl}-1-methylpyridinium methylsulfate, 2-{(4E)-4-[4-(dimetbylamino)benzylidene]-3-methyl-5-oxo-4,5-dihydro-1H- pyrazol-1-yl}-3-methyl-1,3-benzothiazol-3-ium methylsulfate, 2-[(4E)-4-(4-hydroxybenzylidene)-3-methyl-5-oxo-4,5-dihydro-1H-pyrazol-1-yl]-1-methylpyridinium methylsulfate, 2-[(4E)-4-(4-hydroxybenzylidene)-3-methyl-5-oxo-4,5-dihydro-1H-pyrazol-1-yl]-3-methyl-1,3-benzothiazol-3-ium methylsulfate, 2-[(4E)-4-(4-hydroxy-3-methoxybenzylidene)-3-methyl-5-oxo-4,5-dihydro-1H-pyrazol-1-yl]-1-methylpyridinium methylsulfate, 2-[(4E)-4-(4-hydroxy-3-methoxybenzylidene)-3-methyl-5-oxo-4,5-dihydro-1H-pyrazol-1-yl]-3-methyl-1,3-benzothiazol-3-ium methylsulfate, 2-((4E)-4-{[4-(dimethylamino)-1-naphthyll-methylene}-3-methyl-5-oxo-4, 5-dihydro-1H-pyrazol-1-yl)-1-merhylpyridinium methyl-sulfate, 2-((4E)-4-{[4-(dimethylamino)-1-naphthyl]methylene}-3-methyl-5-oxo-4,3-dihydro-1H-pyrazol-1-yl)-3-methyl-1,3-benzothiazol-3-ium methylsulfate and 2-((4E)-4-{(2E)-3-[4-(dimethylamino)phenyl]-2-propen-1-ylidene}-3-methyl-5-oxo-4,5-dihydro-1H-pyrazol-1-yl)-3-methyl-1,3-benzothiazol-3-ium methylsulfate.

* * * * *